(12) United States Patent
Peterson

(10) Patent No.: US 7,308,392 B2
(45) Date of Patent: Dec. 11, 2007

(54) PROCESSES AND SYSTEMS FOR PREDICTING BIOLOGICAL SPECIES INVASIONS

(75) Inventor: Andrew Townsend Peterson, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 666 days.

(21) Appl. No.: 10/167,884

(22) Filed: Jun. 12, 2002

(65) Prior Publication Data

US 2003/0023416 A1 Jan. 30, 2003

Related U.S. Application Data

(60) Provisional application No. 60/297,520, filed on Jun. 12, 2001.

(51) Int. Cl.
*G06G 7/48* (2006.01)
*G06G 7/58* (2006.01)

(52) U.S. Cl. .................. 703/11; 703/2; 703/6

(58) Field of Classification Search ............... 703/2, 703/6, 11
See application file for complete search history.

(56) References Cited

U.S. PATENT DOCUMENTS

2003/0040895 A1* 2/2003 Porter et al. ................ 703/11

OTHER PUBLICATIONS

"DesktopGARP". Printed Oct. 31, 2005. http://www.specifysoftware.org/informatics/Informaticsdesktopgarp/.*
"DesktopGarp Homepage". Printed Oct. 31, 2005. End User License Agreement dated Feb. 25, 2002. http://www.lifemapper.org/desktopgarp/.*
Chornesky, E. et al. "Science Priorities for Reducing the Threat of Invasive Species to Sustainable Forestry." BioScience. Apr. 2005. vol. 55, No. 4, pp. 335-348.*
Hart, D. and R. Gardner. "A Spatial Model for the Spread of Invading Organisms Subject to Competition." Journal of Mathematical Biology. 1997. vol. 35, pp. 935-948.*
Heidorn, P. et al. "Biodiversity and Biocomplexity Informatics: Policy and Implementation Science Versus Citizen Science." Proc. 2nd ACM/IEEE-CS Joint Conf. on Digital Libraries. Jul. 13-17, 2002.pp. 362-364.*
"Species Analyst". Date: Jun. 30, 2003. http://speciesanalyst.net/index.html.*
"Colorado Invasive Species Mapping Project." Undated. Printed Oct. 28, 2005. http://invasivespecies.nbii.gov/projects/coloradomapping.html.*
Andow, D.A. "Spread of Invading Organisms." Landscape Ecology. 1990. vol. 4, Nos. 2/3. pp. 177-188.*
"Jackknife" EPA Statistical Primer. Last updated: May 10, 2005. http://www.epa.gov/bioindicators/primer/jackknife.html.*
Stockwell, D. and Peters, D. "The GARP Modeling System: Problems and Solutions to Automated Spatial Prediction." International Journal of Geographic Information Systems. 1999. vol. 13, pp. 143-158.*

(Continued)

*Primary Examiner*—Paul Rodriguez
*Assistant Examiner*—Ayal Sharon
(74) *Attorney, Agent, or Firm*—Blackwell Sanders LLP

(57) ABSTRACT

Methods and systems are disclosed for predicting species invasions. Native species occurrence information and native environmental information are received. At least one ecological niche model is formulated based on the native species occurrence information and the native environmental information. Target environmental information corresponding to an alternative geography is received. The ecological niche model is projected onto the alternative geography to predict characteristics of an invasion of the species.

18 Claims, 4 Drawing Sheets

OTHER PUBLICATIONS

Stockwell, D. and Noble, I. "Indication of Sets of Rules from Animal Distribution Data: A Robust and Informative Method of Analysis." Mathematics and Computers in Simulation. 1992. vol. 33, pp. 385-390.*

Peterson, A. Townsend and David A. Vieglais. "Predicting Species Invasions Using Ecological Niche Modeling: New Approaches from Bioinformatics Attack a Pressing Problem." BioScience. May 2001. vol. 51, No. 5, pp. 363-371.*

Peterson, A. Townsend et al. "Effects of Global Climate Change on Geographic Distributions of Mexican Cracidae." Ecological Modelling. 2001. vol. 144, pp. 21-30.*

The Internet Archive WayBackMachine search results for http://biodiversity.sdsc.edu/cgi-bin/BSW/screen.cgi, printed Oct. 31, 2005.*

"Welcome to Biodiversity Species Workshop V1.1 User BSW12376." Dated Apr. 10, 2001.*

Sharov, A. et al. "Bioeconomics of Managing the Spread of Exotic Pest Species with Barrier Zones." Ecological Applications. 1998. vol. 8, pp. 1-47, Dated Nov. 14, 2005.*

Sharov, A. et al. "Optimizing the Use of Barrier Zones to Slow the Spread of Gypsy Moth in (Lepidoptera: Lymantriidae) North America." Journal of Economic Entomology. 1998. vol. 91, pp. 165-174.*

Higgins, S. et al. "Using a Dynamic Landscape Model for Planning the Management of Alien Plant Invasions." Ecological Applications. 2000. vol. 10, Issue 6, pp. 1833-1848.*

Powell, J. "Spatio-Temporal Models in Ecology;an Introduction to Integro-Difference Equations." Apr. 9, 2001. http://www.math.usu.edu/~powell/wavclass/labs.pdf.*

* cited by examiner

US 7,308,392 B2

PROCESSES AND SYSTEMS FOR PREDICTING BIOLOGICAL SPECIES INVASIONS

This utility application claims the benefit of Provisional Application No. 60/297,520, filed Jun. 12, 2001.

The invention was made with U.S. Government support awarded by the National Science Foundation (DBI-9808739), and the Government has certain rights in the invention.

BACKGROUND OF INVENTION

Invasive species throughout the world present several widely recognized problems. There are ongoing efforts to prevent introduction of invasive species and to control populations of the harmful invaders. Invading species cause significant economic, ecological, and human health effects. Invaders disrupt natural systems, cause the extinction of native species, compromise transportation and agriculture, and damage natural resources. Further, no systematic, proactive approach to combating invasive species is available. Invasive species are dealt with on a one-at-a-time, reactive basis, and those who would solve problems associated with the invaders seem to be always a step behind.

Scientific approaches to understanding species invasions have developed along several lines, but most have been frustrated by the complex and unpredictable nature of such invasions. Specifically, it is difficult to predict which species will invade and which invaders will become serious problems. For example, considerable effort has been expended in outlining characteristics of species likely to invade, or of invaders likely to become pests. Another line of inquiry and effort has focused on modeling spatial patterns of range expansion after initial invasion. In spite of significant research, an effective approach to understanding species invasions is lacking and desperately needed.

Existing approaches to the challenges presented by species invasions are reactive in nature, and for that reason will always be "catching up" to the most recent problem. Species that have managed to invade a particular region become the focus of intense activity and attention, and solutions are designed to eradicate the species, usually in the form of measures of control and abatement. This scenario, however, does not prevent invasions, and will perpetually lag behind the most recent invasion.

SUMMARY OF INVENTION

Methods and systems consistent with the present invention utilize biodiversity informatics and quantitative geography to identify portions of a landscape that are habitable for a particular invading species. Information on geographic distributions in the form of primary point-occurrence data is harvested from biodiversity information sources, niches of species are modeled in ecological space, and niches are projected onto potentially invaded landscapes. This modeling procedure offers the advantage of being able to outline the possibility of an invasion prior to the species' actual introduction. Given that introductions and the negative effects of a particular invasion are difficult to predict, the present invention provides a way to build biota-wide sets of projections to examine risks of species invasions for all species from a particular region. In this way, the reactive nature of known methods is replaced by a proactive, predictive approach.

BRIEF DESCRIPTION OF DRAWINGS

These and other inventive features and advantages appear from the following Detailed Description when considered in connection with the accompanying drawings in which similar reference characters denote similar elements throughout the several views and wherein.

DETAILED DESCRIPTION

Figure 1:
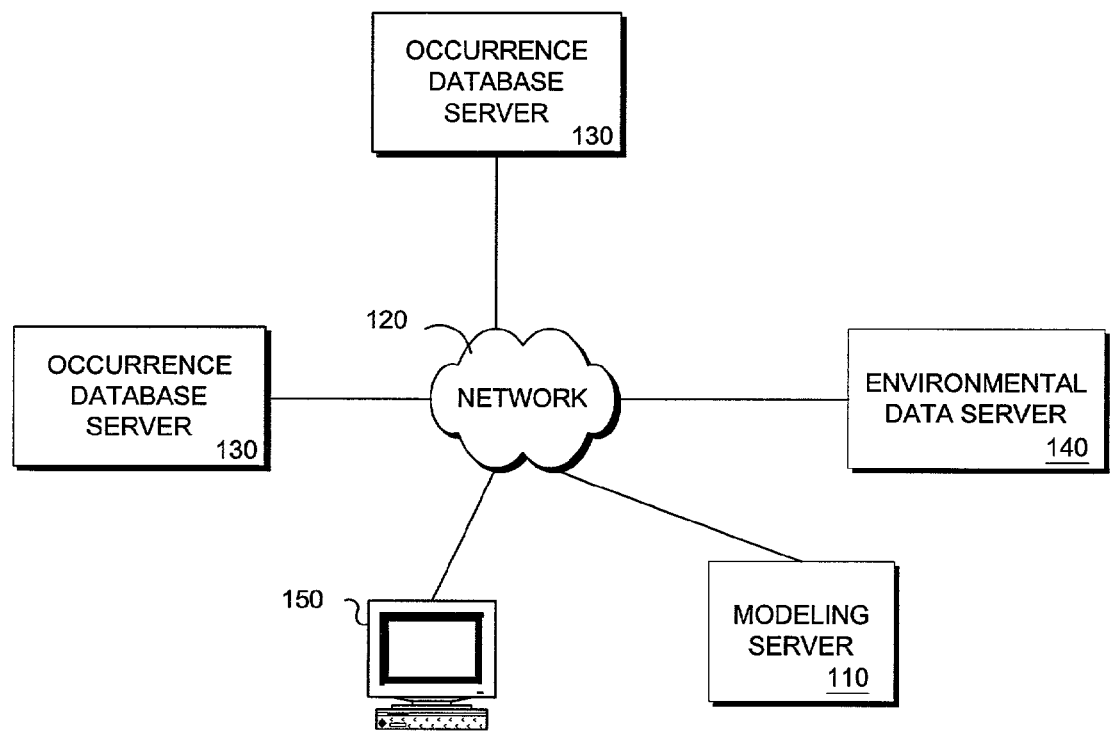
FIG. 1 is schematic block diagram of a distributed network in which methods consistent with the present invention can be practiced.

The impressive ability of species to invade areas outside of their native distributions is associated with evolutionary characteristics of ecological niches. An ecological niche is the set of environmental factors that determine where a species can maintain populations. Niche models are projected onto landscapes in the dimensions in which the niche has been defined. Consequently, the ecological limits of a species' geographic distribution can be projected into geographic dimensions to predict where a species will be able to maintain populations.

Ecological niche models are constructed using point occurrence information records, such as data associated with specimens, in a scientific collection, that identify a particular species at a particular location. Point occurrence information is presently available in from various dispersed sources, many of which are constrained by institutional and national boundaries. Much biodiversity information is stored in the form of scientific collections across North America and Europe. This information is often not computerized, and is considered property of individual institutions. Hence, access to such a collection frequently must be obtained on a one-by-one basis, rendering the process of obtaining sufficient point information a laborious task. However, automated methods of obtaining point occurrence information can be used, for example, an online resource entitled the Species Analyst, available at http://speciesanalyst.net, provides an infrastructure that allows search, retrieval, and analysis of biodiversity data, including information from various institutions regarding diverse taxonomic groups. Further, using various information retrieval standards, such as the ANSI/NISO Z39.50 standard, facilitates accessing bibliographic and geospatial information.

In one embodiment, niche dimensions are chosen to be relevant to geographic distributions, rather than to local distributional issues such as microhabitat or substrate selection. Hence, niche dimensions modeled are those usually considered in geographic limitation of species-temperature, precipitation, elevation, and vegetation These ecological requirements can be divided into fundamental and realized ecological niches: the former representing the base ecological capacity of the species, and the latter incorporating the effects of interactions with other species.

Modeling ecological niches involves developing a multi-dimensional view of the niche of a particular species. Niche models have two types of associated error: omission, which leaves out niche space that is really occupied and commission, which includes niche space not actually occupied. Algorithms for modeling species' ecological niches involve minimizing both omission and commission errors simultaneously. In one embodiment, an algorithm, called the Genetic Algorithm for Rule-set Prediction ("GARP") is used. Individual sub-algorithms with diverse predictive approaches (e.g., multiple regression to predict probability of presence, intersection of ranges along environmental dimensions) are used flexibly in a series of "generations" of rule modification, testing, and incorporation or rejection. Rule "fitness," meaning the predictive accuracy of a rule, is tested by comparing sets of points resampled from both known occurrence points and the background. The result of the genetic algorithm is a set of diverse rules that together define the dimensions of a species' ecological niche. GARP can simultaneously reduce errors of both omission and commission, providing a qualitatively sound estimate of the actual limits of the species' ecological niche. The rule sets describing ecological niches can then be projected onto geographic coverages for regions of interest in the form of either probability surfaces or yes-no predictions.

To facilitate application of GARP to diverse geographic regions, several sets of environmental data ("coverages") are available; although content varies from region to region, typical geographic themes include, for example, precipitation and temperature (averages and extremes), vegetation, elevation, slope, aspect, and soil type. In particular, fine-resolution data are available for the United States, North America, Mexico, Australia, West Africa, Canada, Maine, and China, and a coarser-resolution data set is available for global coverage. Users paste geographic coordinates of species' occurrence points into a form, set model parameters, and run GARP to build an ecological niche model that identifies habitable ecological space and can be used to predict distributions in regions where the species has not yet invaded. Analytical results are output in the form of sets of model rules, map images, and Geographic Information Systems ("GIS") readable grids, making results usable in a variety of applications.

GARP models can be put to several tests for robustness and accuracy. Tests assessing robustness to variation in density of environmental data and occurrence data sample size have indicated that approximately 4-8 environmental data sets and approximately 10-30 occurrence points are generally sufficient to achieve maximum predictive accuracy for a given species.

A general scheme that can be used to test GARP model predictions is that of setting aside random samples of known occurrence points prior to model formulation. Training data are used as the basis for the model in GARP, and test data are then used to assess its predictive ability. Test data (the sample set aside) can be overlain on the prediction, and numbers of points successfully predicted, compared statistically with those expected at random. These approaches can be used on the species' native distributional area to assure that the model developed has significant predictive power. GARP models provided highly accurate (greater than approximately 90% of points correctly predicted) predictions of test data, and were significantly more accurate than random in predicting independent test data points for 22 of 25 Mexican bird species and all of 39 U.S. bird species.

Further, an ecological model can be projected onto landscapes that could potentially be invaded. That is, using the same set of geographic rules or coverages, the ecological niche model is projected onto the landscape of interest in the study. The projections can be tested, if an invasion has already begun.

Consistent with the present invention, there are several methods for applying ecological niche models to a landscape of interest. A direct but time-consuming, method is to apply a derived rule set manually to a parallel set of coverages in the test region. This procedure provides a prediction specifically in terms of the region of special interest. A simpler approach is to develop the ecological model on a set of coverages that extend across both the native and potentially invaded regions. In this embodiment, a tool such as GARP provides a prediction in the test region directly.

FIG. 1 is schematic block diagram of a distributed network in which methods consistent with the present invention can be practiced. A modeling server 110, which is preferably a general purpose computer programmed to formulate ecological niche models is connected to a network 120. In one embodiment, the modeling computer is a PC-type computer, with for example 1 GB of RAM, a reasonably large hard disk, and a CD burner. Further, Microsoft™ Excel, a spreadsheet program, is optionally used in assembling data sets for analysis in connection with the present invention.

The network 120 is preferably the Internet, but it is understood that other types of networks can be used without departing from the scope of the invention as disclosed herein. In one embodiment, the network 120 is preferably an optical fiber based T1 or faster connection, but slower lines can be functional. The modeling server 110 receives information from an occurrence database server 130. The occurrence database server preferably contains point occurrence information corresponding to various species. In one embodiment, the occurrence information is stored in an Oracle™ database. Further, the modeling server 110 receives environmental information from an environmental data server 140, which contains ecological and/or environmental information about geographical locations such as landscapes. In one embodiment, a Geographic Information Systems ("GIS") program is used, preferably an ESRI product (ArcView or Arc/INFO), but other programs can be used as well.

In one embodiment, a client computer system 150 accesses biodiversity information from the modeling server 110 over the network 120. In an alternative embodiment, the modeling server 110 is used directly by an operator to perform ecological niche modeling.

Figure 2:
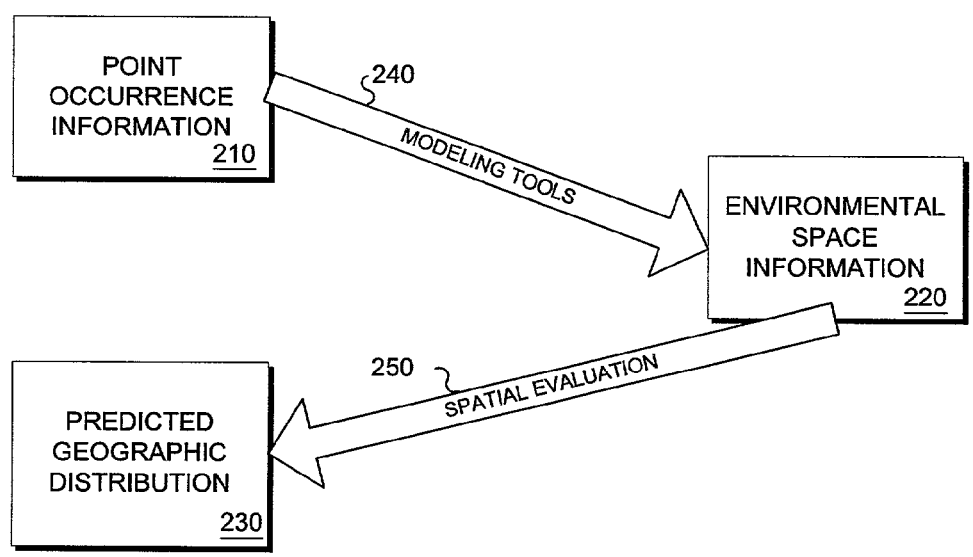
FIG. 2 is a schematic diagram illustrating a transformation of point occurrence information into a predicted geographic distribution.

FIG. 2 is a schematic diagram illustrating a transformation of point occurrence information into a predicted geographic distribution. Point occurrence information 210 is used in connection with modeling tools 240 to formulate models that can predict the range of an invasive species on an arbitrary landscape. Information in the biodiversity world is available in various forms. In some cases, biodiversity information is published, in the form of monographs of taxa, museum catalogues, scientific descriptions, and studies. Specifically, point occurrence information places a species in a particular place at a particular point in time.

Point occurrence information includes several types of information, some of which are primary in nature (i.e., resulting directly from the presence of a species in a particular place), whereas others are secondary (i.e., based on some other set of information. Examples of primary sources include specimens in natural history museums, observations of species, and other direct evidence of species presence (e.g., tracks or scats). Examples of secondary sources include, for example, distributional atlases, range maps, and natural history descriptions. Primary information is preferred and often exists in abundance. Secondary information can introduce sources of bias into results is often unavailable or incomplete for the great majority of taxa.

Even among primary information, data quality can vary significantly. Accordingly, vouchering of specimens is helpful. Natural history museum specimens uniquely provide this critical feature, because a specimen can always be rechecked and reidentified, if necessary, whereas an observation, or even photos or tissue samples cannot be rechecked. New invasive species are often quite difficult to identify, being unknown in the area in question and often difficult to distinguish from a related species.

Information technology has matured to the point that networks integrating data resources seamlessly can be developed on a global scale. In strong contrast to previous, centralized, database systems, modern information technology is moving strongly towards distributed models. Centralized data models, still quite common as a means of managing biodiversity data sets, can take many forms: a single investigator's database of the certain parameters of a particular species, a single collection database, or a clearinghouse for a broad scale survey and inventory project.

Distributed database systems are useful in providing point occurrence information. A distributed model makes possible many exciting design innovations and provides a dimension of redundancy to networks. Institutions retain ownership and possession of their data resources. Information is maintained by institutions that house primary documentation (e.g., specimens), keeping data current with, for example, changes in specimen identification. In fact, data resources can be updated automatically to assure currency on an up-to-the-minute basis, if such is desired. Redundancy of access points and the distributed nature of the network splits up network traffic and query processing into many small questions, avoiding bottlenecks and problems with network traffic. Problems at one point in the network do not influence other sectors of the network, making the network resilient to problems that might cause wholesale failure in a centralized database system.

Much biodiversity information is organized in an ad hoc manner. Many scientific specimens were accumulated incidentally or haphazardly over decades or centuries of sampling. Both species and places are almost always characterized by extremely biased frequency distributions. Even carefully designed sampling schemes, such as the U.S. Breeding Bird Survey, are constrained by accessibility, creating other types of bias (e.g., sampling valleys and not mountain peaks). These biases are quite simply part of life in the world of biodiversity information, and so should be taken into account.

A first step can be that of consideration of these biases as information is being assembled. A source focused on the mammals of Kenya may be very helpful in describing lion distributions, yet it will certainly vastly underestimate the species' distributional possibilities, given the broad range of the species throughout Africa and southern Asia. Accordingly it is beneficial to assemble primary point occurrence data that are reasonably uniformly distributed across the species' geographic distribution, or at least not consistently correlated with environmental gradients.

A useful process involves balancing the occurrence data across regions. Sometimes, biases are unavoidable and information is not available in a uniform or random sampling schema. In such cases localities can be subsampled. Subsampling can be performed in connection with a random number generator, so that further biases are avoided. In one embodiment, an arbitrary framework is applied to structure the subsampling: that is, a latitude-longitude grid system, state or county boundaries, ecoregions, or whatever makes sense in a particular situation can be used to balance sampling intensity across regions.

In order to map species' potential geographic distributions conveniently, input data is preferably provided in a consistent reference in geographic space. In one embodiment, this reference will be in the form of latitude and longitude coordinates. The standard in geographic information systems is to express latitude and longitude as decimals. Latitude is positive in the northern hemisphere, and negative in the southern hemisphere. Longitude is positive in the eastern hemisphere, and negative in the western hemisphere. When these geographic coordinates are expressed in alternate forms, most frequently as degrees, minutes, and seconds, decimal degree values are preferably calculated therefrom.

Geographic references associated with occurrence information are frequently textual in nature. Generally, information on country ("United States"), state or province ("Kansas"), county or municipality ("Douglas County"), named place ("Lawrence"), and directions from that named place ("15 miles west along the Kansas River") will be provided, although older records are often less precise. These textual geographic references are preferably translated into geographic coordinates for analysis.

In one embodiment, georeferencing is automated. In an alternative embodiment, georeferencing is performed manually. Useful resources include the following: maps and atlases in paper form are available for the whole world at various spatial scales of resolution at map libraries in most major cities. Gazetteers or compilations of named places and their geographic coordinates are available for most countries of the world were compiled by the United States Central Intelligence Agency. Regional compilations include the Ornithological Gazetteers series published by the Museum of Comparative Zoology, Harvard University, for all countries in South America. Finally, many countries have their own gazetteers or catalogues of named places.

Further, Internet resources are available to facilitate georeferencing. The Geographic Names Information Server ("GNIS") is one source of localities in the United States. On a worldwide scale, clearinghouses for national or regional gazetteers can be used. Georeferenced data is optionally assembled in a database or spreadsheet.

Environmental space information 220 is obtained, for example from the Hydro1K elevational data set provided by the U.S. Geological Survey. Alternative sources include, for example, the climate data provided by the Intergovernmental Panel on Climate Change ("IPCC") and the global land cover database distributed by the U.S. Geological Survey.

In one embodiment, a set of coverages is received from IPCC and Hydro1K, including, for example, elevation, slope, aspect, annual mean precipitation, annual mean maximum temperature, annual mean temperature, annual mean minimum temperature, daily temperature range, freeze days, wet days, and solar radiation. The coverages are gridded to a resolution of 0.1°×0.1°, which is about 10×10 km grid of cell squares across the entire world.

To extract coverage sets from available data sets, an ArcView Avenue script is preferably employed, that, for example, identifies and exports coverage sets according to the specifications of the user. In one embodiment, a user identifies a region or regions to be studied, by means, including, for example: (i) an Arc shape file with a single polygon that outlines the region to be analyzed; (ii) a rectangle drawn in the view in which the coverages are loaded; or (iii) user-input bounding coordinates. Further, the user optionally provides a desired resolution, in, for example, decimal degrees, to which output coverages are desired.

Further, spatial evaluation techniques are used to produce a predicted geographic distribution 230 based on rules generated in connection with the point occurrence information.

Figure 3:
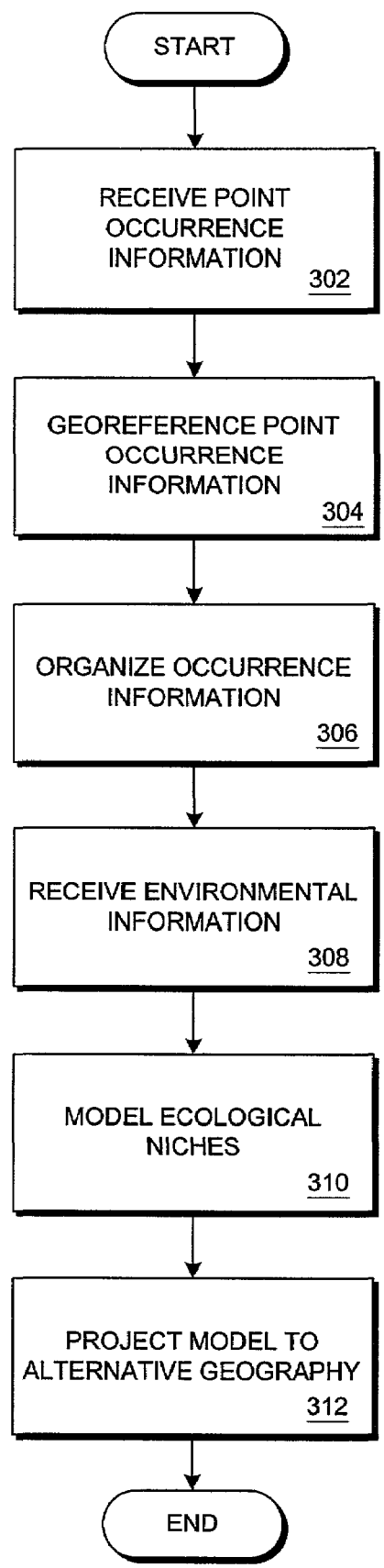
FIG. 3 is a flow diagram illustrating a process of projecting an ecological niche model onto alternative geographies.

FIG. 3 is a flow diagram illustrating a process of projecting an ecological niche model onto alternative geographies. First, point occurrence information is received (stage 302). In one embodiment, the point occurrence information can be obtained by manual observation or other means, as described herein, of obtaining point occurrence information.

Next, the point occurrence information is georeferenced, meaning the geographic coordinates are converted or calculated (stage 304). In one embodiment, the point occurrence coordinates are represented as two real numbers in digital floating point number format.

Next, occurrence information is optionally organized (stage 306). In one embodiment, occurrence data is organized in Microsoft Excel tables with, for example, columns including: species, longitude, and latitude. In this embodiment, latitude and longitude follow the decimal degree conventions regarding hemispheres. In this embodiment, records are sorted by species.

Next, environmental information is received (stage 308). Ecological or environmental data sets provide the dimensions of the ecological niches to be modeled. Useful selection criteria include: whether the coverages are continuous across the entire study region and whether the same coverages are available for both native and invaded ranges.

Next, ecological niches are modeled based on the point occurrence information (stage 310). Various tools can be used to develop these ecological niche models. For example, one tool, BIOCLIM, which is available on the World Wide Web involves intersecting the ranges inhabited by species along each environmental axis (e.g., 1000-1500 m elevation×100-200 mm of rainfall×20-22° C. annual mean temperature). Logistic regression models can be used as well as general linear models, distance-based algorithms, and regression tree analyses.

In one embodiment GARP is used. GARP includes several inferential tools in an iterative, artificial-intelligence-based approach. Occurrence points are resampled evenly to create training and test data sets (1250 points in each set). GARP works in an iterative process of rule selection, evaluation, testing, and incorporation or rejection: first, an inferential tool is chosen from a set of possibilities (e.g., logistic regression, bioclimatic rules), and then is applied to the training data and a rule developed; rules may evolve by a number of means (e.g., truncation, point changes, crossing-over among rules) to maximize predictivity. Predictive accuracy is then evaluated based on 1250 points resampled from the test data and 1250 points sampled randomly from the study region as a whole. The change in predictive accuracy from one iteration to the next is used to evaluate whether a particular rule should be incorporated into the model, and the algorithm runs either 2500 iterations or until convergence. GARP models provide an efficient means of modeling species' ecological niches, and for projecting those models onto geography in the form of maps, which are testable hypotheses of distributional potential.

Regarding errors in predictivity, in some areas, sites that are in actuality within the geographic distribution of the species, are not included in the prediction. This sort of model failure is termed omission error, or a false negative. On the other hand, our prediction also can include some areas that are not, actually, within the species' distribution. Such an error is called commission error, or a false positive.

These two error components can be used to describe many important and salient aspects of the relationship between predictions and species' geographic distributions. Further, the relationship between the two error components can be used to identify the 'best' models, when many replicate models are available. The relationship between omission and commission error components is generally negative, meaning one type of error can be minimized, but at the cost of increases in the other. Moreover, the relationship appears to be concave, meaning that better models are located closer to zero omission. Accordingly, in one embodiment, models that show minimum omission are preferably chosen. In one embodiment, the extreme 10-20% or so of the distribution along the y-axis (omission index) is chosen. Of these minimum-omission models, the median of the commission index (x-axis) is calculated. Next, 10 or so models are chosen that show minimum deviation from this median value. In one embodiment, those models are summed to produce a best-subsets view of the prediction.

Further, the developed model or models are projected onto an alternative geography (step 312). A Windows version of GARP, Desktop GARP, can be used to provide an efficient means for using point-occurrence data and raster GIS coverages summarizing ecological/environmental dimensions to model species' ecological niches and predict potential geographic distributions in alternative landscapes. In the Desktop GARP user interface, the user specifies data sets of point-occurrence information, ecological/environmental data for the native range, and ecological/environmental data for the invaded range, and then sets particular specifications for the characteristics of the analysis desired.

GARP provides output information including three data sets including: results statistics, native range predictions, and 'other' range predictions. In one embodiment, the results file is output both in Microsoft Excel format (.xls) and as an ASCII text file. It is organized with columns representing different fields of data, and rows representing the individual model runs.

Second, GARP projects the ecological model developed in a particular analysis onto the "native" coverage set—the set of ecological-environmental coverages on which the model was based. GARP projections are output in subdirectories, using a file-system hierarchy. For a given model, a projection that is suffixed with "_0" is this native projection. The native projections are often very useful in invasive species applications because they can be used in tests of model quality prior to projection onto other landscapes.

Further, GARP projects the ecological model developed in a particular analysis onto each of the additional coverage sets that are specified for projection (see above). The models are output with suffixes ("_1", "_2", etc.) that match the order in which the coverage sets are listed in the projection list in the GARP user interface.

Figure 4:
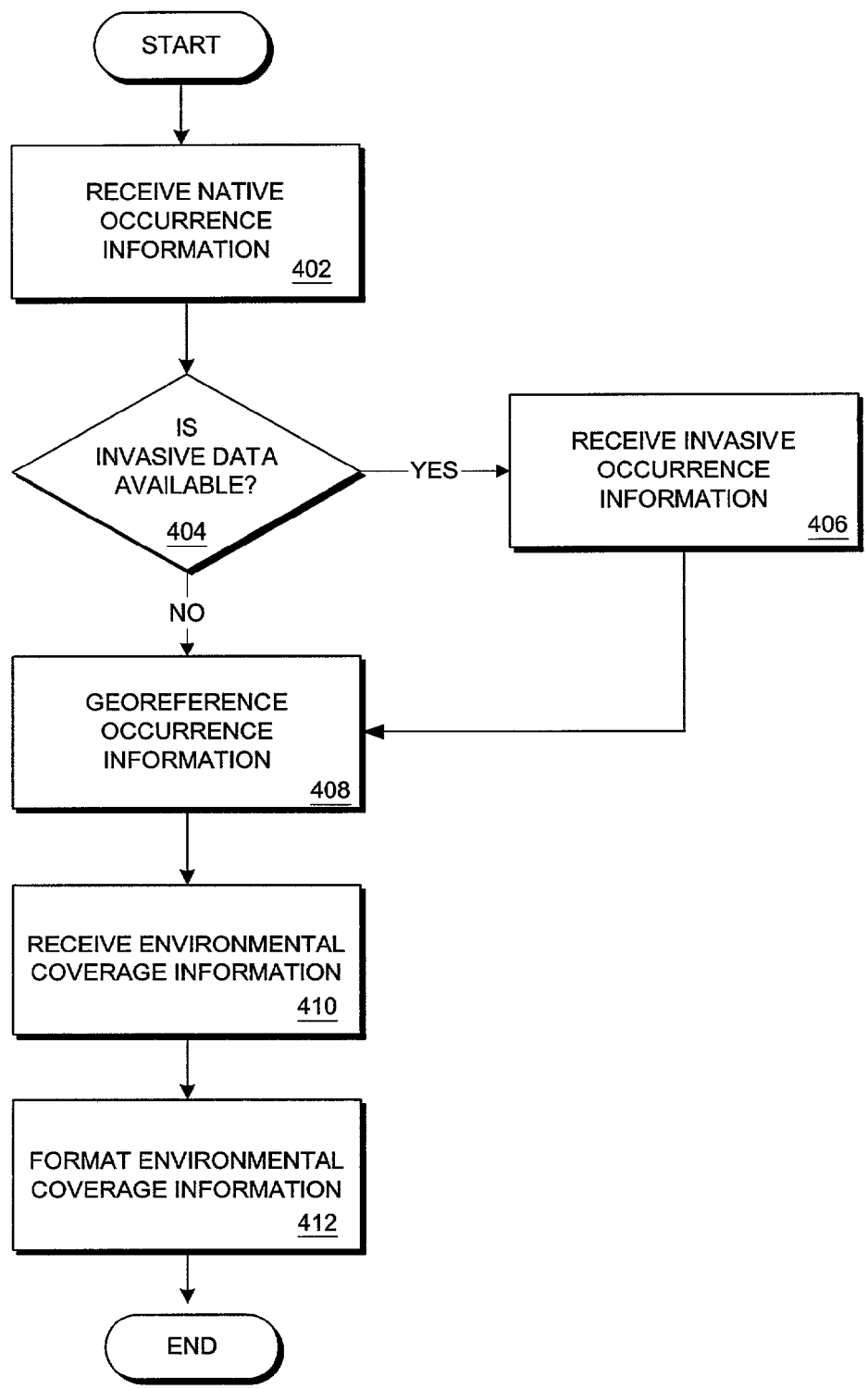
FIG. 4 is a flow diagram illustrating a process of preparing information for use consistent with the present invention.

FIG. 4 is a flow diagram illustrating a process of preparing information for use consistent with the present invention. First, native occurrence information is received (stage 402). Any institution holding biodiversity data, e.g., a database of species' occurrences, can participate as a data server in connection with the Species Analyst, for example. Data is preferably in electronic form, in a platform under which Structured Query Language ("SQL") constructs can be used to query the data, documenting occurrences of species. Further, if an invasion has already begun, then invaded distributional area points can provide an additional means of model validation. In one embodiment, sample sizes include at least about 20-50 unique occurrence points. Occurrence points from native distributions should be spread, as much as possible, across the native distribution, so as to avoid biasing the modeling process.

Point-occurrence data are available from various of sources. A convenient source is the Species Analyst, which yields electronic data in a matter of minutes, whereas other sources focus on taxonomic literature, which require detailed data extraction and computerization. Many museums have placed their electronic databases online for public access. These databases must often be queried one at a time, and data are output in diverse formats, yet the information is still useful. If an invasion has already begun and invasive-range occurrence information is available (stage 404), invasive occurrence can be input similarly to the invaded range information, and received by a modeling computer system (stage 406).

Native and optional invasive occurrence information is georeferenced (stage 408). Occurrence is not infrequently encountered as textual data without quantitative georeferencing (e.g., latitude-longitude coordinates). Nevertheless, large amounts of georeferenced occurrence data are provided in some cases (for example, for marine fishes on Species Analyst). When geographic references are just textual (e.g., "USA, Kans., Douglas County, Lawrence, 5 km east"), however, as often will be the case, translation into latitude and longitude coordinates is necessary.

Several georeferencing approaches can be used, including, for example: (i) hand-georeferencing from maps, (ii) use of electronic gazetteer databases, and (iii) automated georeferencing. A GIS convention that should be borne in mind throughout is that of referring to northern and southern hemispheres as positive and negative latitudes, to eastern and western hemispheres as positive and negative longitudes, and to minutes and seconds as decimal fractions of degrees. In this way, any point on Earth can be identified with just two real numbers.

Hand-georeferencing, although the most time-consuming, provides the greatest opportunity to interpret and quality-control the information that is to be analyzed, and in this sense is preferable. Nevertheless, in some situations it is prohibitively time-consuming given the sheer enormity of the time investment required. Manual georeferencing involves searching for the point occurrence on the finest-scale maps available, and recording the latitude and longitude of the point occurrence. For small data sets with relatively few occurrence points, this approach may prove optimal, as quality of resulting coordinate data can be controlled carefully.

Electronic gazetteers can be used to speed up georeferencing considerably. Such gazetteers are essentially lists of place names for a particular region that carry latitude and longitude data. When modifiers exist (e.g., "5 miles west," "20 road km south"), application of electronic gazetteers becomes more complex as calculation of the latitude and longitude of the modified point involves spherical trigonometry to take into account the different distances that result from the curvature of the surface of the Earth.

It is worth remembering that some electronic gazetteers provide data as degrees-minutes-seconds, often as a 6- or 7-digit number (DDMMSS, or DDDMMSS). These numbers must be parsed into degrees, minutes, and seconds, combined into decimal degrees, and assigned a sign (+ or −) corresponding to hemispheres of occurrence. In one embodiment, environmental coverage information is received, corresponding to the native ranges and to a landscape to be projected (stage 410). Further, the environmental coverage information is optionally formatted in a convenient format (stage 412). In one embodiment, the environmental coverage information is formatted as an ASCII text file.

Figure 5:
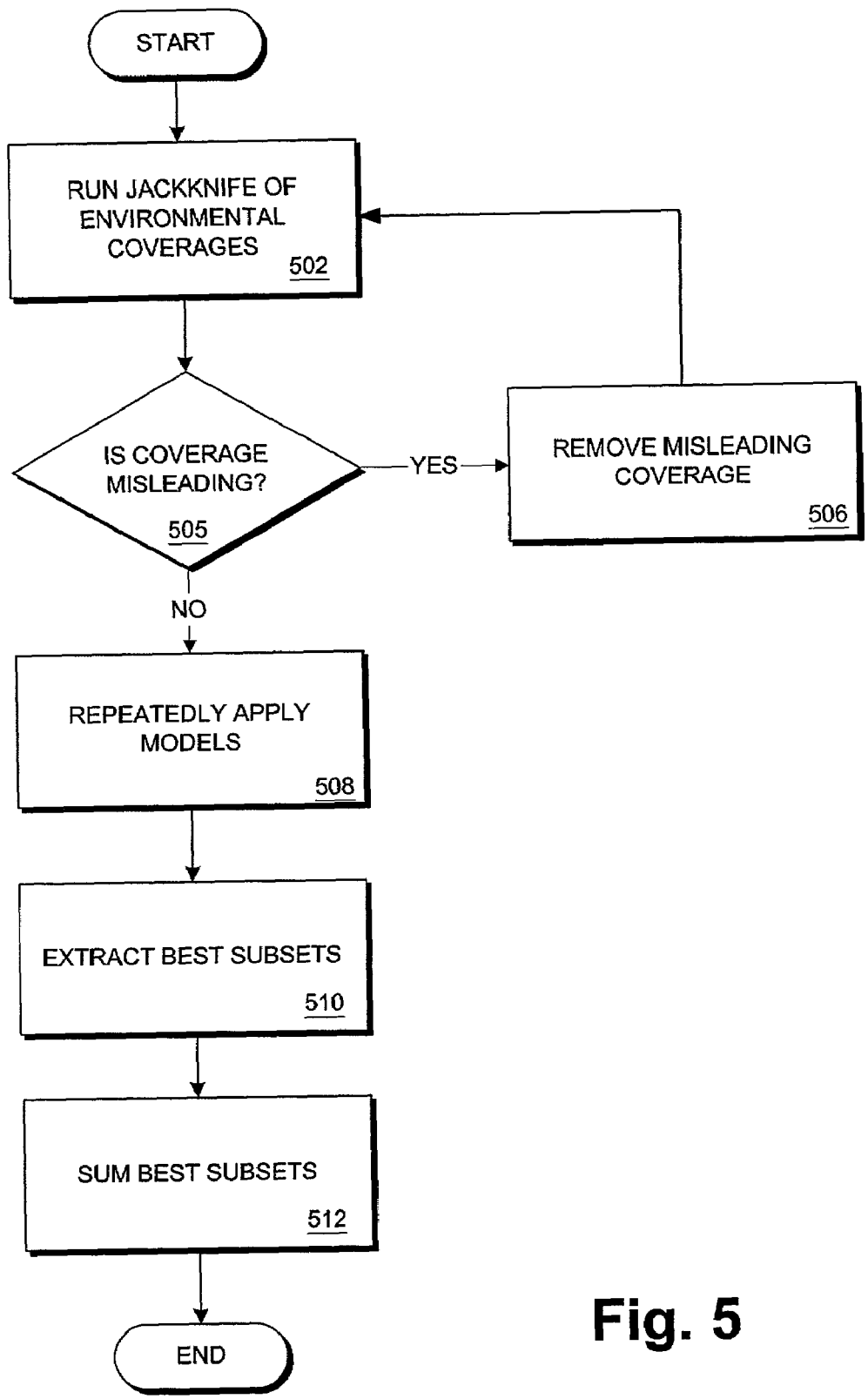
FIG. 5 is a flow diagram illustrating a process of developing an ecological niche model consistent with the present invention.

FIG. 5 is a flow diagram illustrating a process of developing an ecological niche model consistent with the present invention. First a jackknife algorithm is applied to the environmental coverages (stage 502). Accordingly, it is determined whether a particular coverage is misleading, meaning that it causes errors to be introduced into the model. If a particular coverage is misleading, it is removed from an associated list of rules (stage 506). Next, the models are repeatedly applied to environmental information associated with a particular geographic region to generate a large population of replicates (stage 508) and, the best subsets are extracted (stage 510). That is, if 1000 replicate models are developed, some of them will present qualitatively better combinations of omission and commission error, and will genuinely represent better models. The procedure is based on the observations that: (i) models vary in quality; (ii) variation among models involves an inverse relationship between omission and commission error, and (iii) best models (as judged by experts blind to error statistics in the original derivation of the approach) are clustered in a region of minimum omission of independent test points and moderate area predicted (an axis related directly to commission error). The relative position of the cloud of points relative to the two error axes provides an assessment of the relative accuracy of each model. In one embodiment, choosing best subsets of models involves: (i) eliminating all but models that have no omission error based on the independent test points; (ii) calculating the median area predicted present among these zero-omission models (% of the area analyzed); and (iii) identifying models that were closest to the overall median extent.

In one embodiment, at least 10 model predictions are used, but many more (100-200, even) can be useful, out of these models closest to the median. Further, the best subsets are summed to generate an aggregate model reflecting the respective strengths of each of the aggregated models (stage 512).

There are several factors that influence the predictive accuracy of an ecological niche model. First, if a single coverage dominates in the output prediction maps it suggests that the complexities of the ecological landscape are not being taken into account in the development of the model. This problem often results when a mismatch exists in spatial scale of occurrence data and ecological-environmental data—that is, if ecological-environmental data are resolved rather coarsely as compared with the occurrence data, such domination can occur.

Second, poor performance in predicting independent test occurrence data indicates that the model is not capturing the essence of the species' ecological requirements. This type of poor performance can take the form of omitting known occurrences (omission error), or of predicting an area too large (commission error, detectable only if independent test points can be trusted to represent most of the environments and regions in which a species is found).

Various strategies are available for further refining models. When input occurrence data (both training and test data sets) are biased ecologically or geographically, the input data can be balanced, involving subsampling of the data set to reduce or eliminate the bias. That is, for example, the known occurrence data may be biased towards the southeastern portion of a species' distribution, with only scattered points available for the remainder. This situation, when analyzed with GARP, given the bias in sampling intensity strongly correlated with environmental gradients, will produce a prediction that is similarly biased towards the region of most intense sampling. The scattered points, in this example, in the northeastern United States, would be left out of the prediction without subsampling to abate the bias. An appropriate procedure to remedy this situation is to subsample the over represented regions based on some criterion independent of the ecology of the sampled regions.

A further approach is jackknifing coverages for inclusion in the modeling exercise. That is, the independent nature of native distributional areas and areas of potential invasion can be exploited. Model parameters and data sets can be fine tuned based on the native distributional area without biasing the prediction on the potentially invaded region. The use of this approach is based on the premise that some of the input environmental coverages may be correlated with presence and absence of a species not for reasons important to the species' ecological niche—this false association will be reflected in poor performance (omission error, in particular) when evaluated by independent test points.

An effective step towards detection of such false associations is jackknifing the inclusion of coverages in a first round of modeling, based only on the native range of a species. A jackknife of N-1 (or N-2 or more, if the number of layers is not large) can be selected (this setting will eliminate each of the coverages systematically from analysis). Then, a results file is opened, and a correlation matrix calculated between the presence and absence of each data layer and the extrinsic omission error. The values of these correlations range from −1 to 1: a high negative value indicates a coverage for which absence in analysis is associated with higher omission error, whereas a high positive value (e.g., r>0.08, approximately) indicates a coverage for which presence is associated with higher omission error. These latter coverages should be eliminated from further analysis. Several rounds of jack-knifing will reduce the set of input coverages to a set that is uniformly associated with better model performance.

Consistent with novel methods and systems practiced in connection with the present invention, species invasions can be predicted based on ecological niche models. Such methods and systems involve: (i) preparing data; (ii) developing models; and (iii) applying the developed models. Preparing the data involves: (i) accumulating occurrence data for native geographic distribution of a species; (ii) accumulating occurrence data for invaded geographic distribution of species, if the analysis is retrospective; (iii) georeferencing data to latitude-longitude points; (iv) organizing latitude-longitude coordinates in a spreadsheet; (v) assembling base environmental coverages via sources of geospatial information; and (vi) exporting environmental data sets as ASCII raster grids. Model development involves: (i) running a jackknife algorithm of coverages, omitting as many coverages and running as many replicate analyses as is feasible, for the native distribution; (ii) evaluating correlations to detect misleading coverages; and (iii) repeating jackknifes and evaluations until no more misleading coverages are found. Further, predicting invasions involves: (i) running 100-1000 replicate models based on final set of environmental coverages, including a projection to invaded distributional areas; (ii) extracting 5-10% of the models as 'best subset'; (iii) summing the best subsets models to produce distributional predictions; (vi) projecting best subsets models to the invaded range and summing to produce a prediction of the potential invaded range; and (v) the model can be evaluated based on test points and invaded region validation points if the examined invasion has begun.

EXAMPLES

Cattle egrets (Bubulcus ibis) were originally restricted to the Old World Tropics in Africa and southern Asia. A flock of this species, however, was blown across the Atlantic Ocean to northeastern South America in the 1950s, where a population became established. Cattle egret populations quickly spread throughout the New World Tropics, and north through Central America and Mexico into the southern United States.

Using 70 historical records from 1958-1988, cattle egret populations in Mexico during their northward invasion were tested to determine whether the spatial extent of their U.S. colonization could be predicted accurately. The ecological niche model for the species in all of North America was based on eight geographic themes, including aspects of vegetation, precipitation, and temperature. The predictions of the model were tested with 673 known occurrence points drawn from the results of the U.S. Breeding Bird Survey ("BBS").

The portion of this model extending into the United States predicts distributional areas across the southeastern states, extending narrowly along the Atlantic seaboard as far north as New York. The interior and western parts of the country are predicted either not to represent appropriate distributional areas or to hold only sparse populations. Overlaying the BBS test occurrence data on the model predictions, it was determined that the model predicted the areas invaded quite well: 5.7% of the country was predicted as potential distributional area, but 42.5% of the U.S. occurrence points were correctly predicted. Using chi-square tests to evaluate the significance of these predictions, probability levels were less than $10^{-200}$, or impossibly successful if not accurately evaluating dimensions of the species' ecological niche.

The House Finch is native to western North America, ranging from the Great Plains west to the Pacific Ocean, and from southern British Columbia south to southern Mexico. Introduced into Long Island, N.Y., in 1940, this species long stayed in the immediate vicinity. In the 1960s, however, it began expanding rapidly throughout New England, and south and west through much of the eastern United States. Eastern and western populations met in the eastern Great Plains in the late 1980s, and the species' distribution appears to have been relatively stable since that time.

In formulating the model, 1313 occurrence points were obtained from the Species Analyst to establish ecological characteristics of the species on its native distribution in the western United States. The developed models predicted most of the concentrations of 883 independent BBS records on the native range, achieving a fair degree of statistical significance. Therefore, the ecological model was successful in predicting the species' native distribution. Further, portions of western North America predicted to hold populations by the models but not corroborated by test data points (e.g., most of Montana), are now being invaded by populations of house finches.

Applying the model to eastern North America, although only 28.6% of eastern North America was predicted to be suitable for house finches, the models correctly predicted 49% of the 1333 test data points. This level of predictivity is unlikely to have occurred by chance, with probability levels below $10^{-55}$. Hence, these models provides a much-improved idea of where this species was likely to invade in eastern North America.

Asian Longhorned Beetle

A recently arrived and particularly worrisome invader in North America currently is the Asian longhorned beetle (Anoplophora glabripennis), the larvae of which damage trees and forests; the geographic extent of its possible invasion of North American forests, however, is unknown. Ecological niche models developed on the species' native range in Asia and projected onto North America that suggest that the species has the potential to invade much of eastern North America, but only limited areas in western North America.

A total of 44 occurrence records for Asian longhorned beetles was obtained, based on specimen localities for the species from China and elsewhere in eastern and southeastern Asia. These records were georeferenced by hand and plotted in ArcView™ version 3.1, available from Environmental Systems Research Institute, Inc ("ESRI"). Four localities were identified as uncertain from the outset, and, given that they constituted spatial outliers when plotted, were eliminated from analysis. Models were built based on 18 geographic coverages representing climatic dimensions drawn from ArcAtlas™ also available from ESRI, including high and low values for annual, January, and July mean temperature and precipitation, solar radiation, snow cover, and frost-free days. Coverages were imported into ArcView and exported as ASCII raster grids with 22×17 km pixels across eastern and southern Asia, and 1×1 km pixels across North America.

To assess model quality, Asian longhorned beetle distributions were modeled in Asia based on half (20 "training points") of the points available, and then model adequacy tested with the other half ("test points"). Equal partitions were chosen five times randomly, and success of the model in predicting the test data set was assessed, compared with success expected if points were distributed randomly, using a chi-square test. That is, the proportional area predicted present multiplied by the 20 points provided expected numbers under a random model. To produce an overall "best" model, however, all 40 points available were used to develop 20 independent models based on the full data set; these maps were summed to produce a graded map of predicted presence, with values ranging from 0 to 20. The 18 climatic coverages were combined with the summed GARP predictions using the "Combine" option. The INFO table associated with this composite coverage allowed visualization of modeled suitability versus availability of combinations for key environmental dimensions. Rule-sets associated with the 20 models for the Asian distribution of the species were used to identify areas in North America that fulfill the modeled ecological requirements of the species, thus predicting a potential geographic distribution in North America. This geographic prediction represents the conjunction of climatic conditions modeled as appropriate for the species on its native range projected onto the potentially invaded range.

In further research, five random equal partitions of the available occurrence data were used to test whether accurate and predictive ecological niche models can be developed for Asian longhorned beetles in climatic dimensions on geographic scales. For the example, each of the 20 independent test points were correctly predicted by the model, but only 33.2% of the region was predicted present, yielding an expected number of 6.6 correct predictions under a random model. Statistical results indicated that models developed for the species were indeed predictive of the species' ecological requirements and potential geographic distribution.

The rule-sets associated with the 20 Asian models were used to identify areas in North America that fulfill the modeled ecological requirements of the species. Patterns of low probability (arctic regions, high mountain regions), intermediate probability (northern regions, western North America, Mexico, and Central America), and high probability (eastern North America) were clear, suggesting that the species would encounter vastly different suitabilities of climate regimes at points across North America. This map was compared with known warehouse detections and actual outbreak distributions in North America. Coincidence with warehouse detections was poor, suggesting that these occurrences are more related to opportunity for arrival than to the suitability of the site for the species. Actual infestations, however, appear to be predicted better: both major sites (Chicago and New York) are within the general prediction of 75% of models, but are too few to attempt statistical testing.

The climate-based maps were compared with a risk map developed by the U.S. Forest Service based on forest types known to be vulnerable to the species in its native range. This latter map emphasizes the northeastern fringe of the United States from Minnesota to Maine, whereas results predicted in connection with the present invention focus somewhat farther south. However, many of the same trees (e.g., maple, elm, birch) on which the Forest Service map focused are planted as ornamentals and shade trees far south of their native range, in cities and towns throughout eastern North America. Hence, even in the absence of vulnerable native forest, climatic conditions are appropriate for the species throughout much of the eastern United States and southeastern Canada and appropriate tree species are available. The predictions do require the explicit assumption of no evolution in niche characteristics of the species as part of the invasion, and although niche evolution is often conservative over such time spans, this assumption must be borne in mind.

The analyses suggest that the area of greatest danger of Asian longhorned beetle invasion in North America is not, as might be expected, along the west coast, where Asian shipping volume is greatest. Rather, the eastern portion of the country is most vulnerable, because abundant appropriate habitat lies close to major shipping ports. Although some danger does still exist from secondary transportation (e.g., by truck or rail) in the west, the clear priority for combating this invasive is in the east, particularly the area just south of the Great Lakes. Modeling suitability of habitat combined with opportunity for invasion allows mitigation efforts to be concentrated in areas most vulnerable to invasion, and may save time, effort, and money, as well as improving possibilities of successfully combating the invasion.

Barred Owl

The Northern Spotted Owl (Strix occidentalis) is ecologically restricted to old growth forests, ranging from the Pacific Northwest south through montane areas to southern California. Given widespread habitat destruction across much of its geographic distribution and consequent population declines, the species was placed on the U.S. Endangered Species List in 1990, which afforded it new measures of protection, including redesign of timber concessions on public lands. With the species' high-profile status and abundant population and demographic data, it has also become a touchstone for many theoretical treatments in conservation biology.

Recently, however, an additional peril for the Northern Spotted Owl has appeared. Its eastern North American congener, the Barred Owl (Strix varia), has been extending its range westward since the 1960s, jumping over much of the Great Plains, Rocky Mountains, and intermontane region to arrive in the Pacific Northwest. Where Barred Owls have arrived in areas inhabited by Spotted Owls, owing to the former's more aggressive nature, the latter has generally been displaced. Hence, portions of the Spotted Owl's distribution may be in danger even when habitat fragmentation is not a factor. Methods and systems consistent with the present invention make possible prediction of potential species invasions via modeling of ecological niches based on primary point-occurrence data.

A sample of 138 Barred Owl and 27 Spotted Owl specimen records drawn from The Species Analyst from the species' native distribution was the basis for our inferences. Predictive models were tested using 1116 Barred Owl points drawn from the U.S. Breeding Bird Survey results. Geographic/ecological themes used in analyses consisted of eight coverages (life zones, soil class, annual mean temperature, annual mean precipitation, vegetation class, vegetation type, wetlands, and world ecosystems. To allow analyses at continental scales, each coverage was generalized to a pixel resolution of 50×50 km.

The ecological niche model predicted potential distributional areas for Barred Owls broadly across eastern North America, and sparsely in the Pacific Northwest. In all, 1032 of 1116 (92.5%) independent test points from the U.S. Breeding Bird Survey 6 were successfully predicted. Given 49.8% of the lower 48 United States predicted present, 556 points would have been successfully predicted at random, indicating significant predictive ability of the niche model. In fact, areas predicted present but not populated by Breeding Bird Survey points are indeed inhabited. Although fewer distributional points were available for the Spotted Owl, the distributional prediction developed from these data reflected well the known distribution of the species in the Pacific Northwest and California.

Potential distributional areas of Barred and Spotted Owls both extend through much of the Pacific coastal mountain ranges of North America. Much of the northern portion of the U.S. range of the Northern Spotted Owl (from the Canadian border south to about the latitude of San Francisco Bay) is also inhabitable by Barred Owls, suggesting that Barred Owls could invade much of this portion of the distribution of the Northern Spotted Owl.

The invention claimed is:

1. A computer-implemented method of predicting species invasions, the method comprising:
   receiving native species occurrence information; receiving native environmental information;
   formulating at least one ecological niche model based on the native species occurrence information and the native environmental information;
   receiving target environmental information corresponding to an alternative geography; and
   projecting the ecological niche model onto the alternative geography to predict characteristics of an invasion of the species.

2. The method as set forth in claim 1, wherein the native species occurrence information includes primary point occurrence information.

3. The method as set forth in claim 2, wherein the primary point occurrence information includes direct evidence of species' presence at a particular location.

4. The method as set forth in claim 1 further includes georeferencing the native species occurrence information.

5. The method as set forth in claim 4, wherein the georeferencing includes automated georeferencing.

6. The method as set forth in claim 1 further including organizing the native species occurrence information.

7. The method as set forth in claim 6, wherein the organizing includes formatting the native species occurrence information into columns characterized by an identification of the species, longitude, and latitude.

8. The method as set forth in claim 1, wherein the native environmental information includes data sets from the Hydro1K elevational data set.

9. The method as set forth in claim 1, wherein the native environmental information includes data sets from the global land cover database.

10. The method as set forth in claim 1 wherein the target environmental information includes data sets from the Hydro1K elevational data set.

11. The method as set forth in claim 1, wherein the target environmental information includes data sets from the global land cover database.

12. The method as set forth in claim 1, wherein the native environmental information includes at least 4-8 sets of geospatial information and the native species occurrence information includes at least 10-30 species occurrence points.

13. The method as set forth in claim 1 further comprising executing a jackknife algorithm in connection with rules associated with the ecological niche model.

14. The method as set forth in claim 13, wherein the ecological niche model is formulated by selecting best subsets of the rules associated with the ecological niche model.

15. The method as set forth in claim 14, wherein the ecological niche model is aggregated by summing the best subsets of the rules associated with the ecological niche model.

16. A method of predicting species invasions, the method comprising:
   receiving native species occurrence information;
   receiving geospatial information associated with native species occurrence information and with a target geographical region;
   developing environmental criteria associated with an ecological niche model based on the native species occurrence information and the geospatial information; and
   projecting the environmental criteria onto the target geographical region to model an invasion of the target geographical region by the species.

17. A distributed computer network for predicting effects of species invasions, the computer network comprising:
   a species occurrence database server;
   a geospatial environment database server; and
   a modeling server having a memory containing computer readable instructions capable of: receiving native species occurrence information;
   receiving native environmental information;
   formulating at least one ecological niche model based on the native species occurrence information and the native environmental information;
   receiving target environmental information corresponding to an alternative geography; and
   projecting the ecological niche model onto the alternative geography to predict characteristics of an invasion of the species.

18. An apparatus operable to predict species invasions, the apparatus comprising:
   means for receiving native species occurrence information;
   means for receiving native environmental information;
   means for formulating at least one ecological niche model based on the native species occurrence information and the native environmental information;
   means for receiving target environmental information corresponding to an alternative geography; and
   means for projecting the ecological niche model onto the alternative geography to predict characteristics of an invasion of the species.

* * * * *